(12) United States Patent
Kalgren et al.

(10) Patent No.: US 8,121,689 B2
(45) Date of Patent: Feb. 21, 2012

(54) PROACTIVE INTERACTIVE LIMITS OVERRIDE FOR IMPLANTABLE MEDICAL DEVICE USER INTERFACE

(75) Inventors: James Kalgren, Lino Lakes, MN (US); Les Peterson, Woodbury, MN (US); Jonathan H. Kelly, Woodbury, MN (US); Hai Huang, Woodbury, MN (US); Gang Wu, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 823 days.

(21) Appl. No.: 11/865,506

(22) Filed: Oct. 1, 2007

(65) Prior Publication Data

US 2009/0088815 A1 Apr. 2, 2009

(51) Int. Cl.
*A61N 1/08* (2006.01)
(52) U.S. Cl. ............... 607/30; 607/32; 607/59; 607/60
(58) Field of Classification Search .............. 607/30, 607/32, 59–60
See application file for complete search history.

(56) References Cited

U.S. PATENT DOCUMENTS

| | | | |
|---|---|---|---|
| 4,208,008 A | 6/1980 | Smith | |
| 4,432,360 A | 2/1984 | Mumford et al. | |
| 4,809,697 A | 3/1989 | Causey, III et al. | |
| 5,159,926 A * | 11/1992 | Ljungstroem | 607/30 |
| 5,215,083 A | 6/1993 | Drane et al. | |
| 5,267,346 A | 11/1993 | Maruyama et al. | |
| 5,292,341 A | 3/1994 | Snell | |
| 5,360,437 A | 11/1994 | Thompson | |
| 5,379,776 A | 1/1995 | Murphy et al. | |
| 5,496,351 A | 3/1996 | Plicchi et al. | |
| 5,507,786 A | 4/1996 | Morgan et al. | |
| 5,523,942 A | 6/1996 | Tyler et al. | |
| 5,549,654 A | 8/1996 | Powell | |
| 5,607,460 A | 3/1997 | Kroll et al. | |
| 5,609,612 A | 3/1997 | Plicchi et al. | |
| 5,620,471 A | 4/1997 | Duncan | |
| 5,636,328 A | 6/1997 | Kautz et al. | |
| 5,693,075 A | 12/1997 | Plicchi et al. | |
| 5,713,937 A | 2/1998 | Nappholz et al. | |
| 5,716,382 A | 2/1998 | Snell | |
| 5,716,384 A | 2/1998 | Snell | |

(Continued)

OTHER PUBLICATIONS

"U.S. Appl. No. 11/380,570, Non-Final Office Action mailed Dec. 22, 2008", 14 pgs.

(Continued)

*Primary Examiner* — Carl H Layno
*Assistant Examiner* — Jennifer Stewart
(74) *Attorney, Agent, or Firm* — Schwegman, Lundberg & Woessner, P.A.

(57) ABSTRACT

An external device includes a communication circuit, a programming interface including a display, and a processor. The processor includes a parameter analyzer to apply a rule to a combination of operating parameter values of the IMD to determine operating parameter interaction. The display includes a first warning that is displayed when the parameter analyzer determines that a combination of operating parameter values entered via the programming interface is not allowed, and a second warning that is displayed when the parameter analyzer determines that a combination of operating parameters values entered via the programming interface is allowable but not recommended. The processor is configured to program the operating parameter values associated with the second warning into the IMD only after a user acknowledgement of the second warning is received from a user via the programming interface.

15 Claims, 7 Drawing Sheets

U.S. PATENT DOCUMENTS

| | | |
|---|---|---|
| 5,722,999 A | 3/1998 | Snell |
| 5,724,985 A | 3/1998 | Snell et al. |
| 5,725,559 A | 3/1998 | Alt et al. |
| 5,749,907 A | 5/1998 | Mann |
| 5,755,736 A | 5/1998 | Gillberg et al. |
| 5,759,199 A | 6/1998 | Snell et al. |
| 5,785,660 A | 7/1998 | van Lake et al. |
| 5,792,204 A | 8/1998 | Snell |
| 5,836,989 A | 11/1998 | Shelton |
| 5,839,989 A | 11/1998 | Saito et al. |
| 5,843,138 A | 12/1998 | Evers et al. |
| 5,891,178 A | 4/1999 | Mann et al. |
| 5,908,392 A | 6/1999 | Wilson et al. |
| 5,978,707 A | 11/1999 | Krig et al. |
| 6,004,020 A | 12/1999 | Bartur |
| 6,016,442 A | 1/2000 | Hsu et al. |
| 6,031,984 A | 2/2000 | Walser |
| 6,045,513 A | 4/2000 | Stone et al. |
| 6,088,618 A | 7/2000 | Kerver |
| 6,091,990 A | 7/2000 | Hsu et al. |
| 6,101,416 A | 8/2000 | Sloman |
| 6,289,248 B1 | 9/2001 | Conley et al. |
| 6,690,972 B2 | 2/2004 | Conley et al. |
| 6,700,097 B1 | 3/2004 | Hsu et al. |
| 6,842,644 B2 | 1/2005 | Anderson et al. |
| 7,003,349 B1 | 2/2006 | Andersson et al. |
| 7,010,349 B2 | 3/2006 | Conley et al. |
| 7,089,221 B2 | 8/2006 | Fromherz et al. |
| 7,191,006 B2 | 3/2007 | Hu et al. |
| 7,272,444 B2 | 9/2007 | Peterson et al. |
| 7,613,672 B2 | 11/2009 | West et al. |
| 2002/0049481 A1 | 4/2002 | Conley et al. |
| 2002/0091308 A1* | 7/2002 | Kipshidze et al. ............ 600/300 |
| 2002/0143372 A1* | 10/2002 | Snell et al. ..................... 607/30 |
| 2002/0156389 A1 | 10/2002 | Kalgren et al. |
| 2003/0125776 A1 | 7/2003 | Turney et al. |
| 2004/0111131 A1 | 6/2004 | Hu et al. |
| 2004/0116982 A1 | 6/2004 | Conley et al. |
| 2005/0010258 A1 | 1/2005 | Peterson et al. |
| 2005/0010388 A1 | 1/2005 | Bagchi et al. |
| 2005/0033385 A1 | 2/2005 | Peterson et al. |
| 2005/0060008 A1* | 3/2005 | Goetz ............................ 607/48 |
| 2005/0060198 A1 | 3/2005 | Bayne |
| 2005/0216064 A1* | 9/2005 | Heruth et al. ..................... 607/3 |
| 2006/0111759 A1* | 5/2006 | Hoyme et al. .................. 607/60 |
| 2006/0241822 A1 | 10/2006 | Yadappanavar et al. |
| 2008/0126968 A1 | 5/2008 | West et al. |
| 2008/0269812 A1* | 10/2008 | Gerber et al. ..................... 607/2 |

OTHER PUBLICATIONS

"U.S. Appl. No. 11/380,570, Notice of Allowance mailed Jun. 24, 2009", 11 pgs.

"U.S. Appl. No. 11/380,570, Response filed Mar. 23, 2009 to Non Final Office Action mailed Dec. 22, 2008", 22 pgs.

"International Application Serial No. PCT/US2007/066237, International Search Report mailed Oct. 4, 2007", 3 pgs.

"International Application Serial No. PCT/US2007/066237, Written Opinion mailed Oct. 4, 2007", 5 pgs.

\* cited by examiner

PROACTIVE INTERACTIVE LIMITS OVERRIDE FOR IMPLANTABLE MEDICAL DEVICE USER INTERFACE

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records, but otherwise reserves all copyright rights whatsoever.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Implantable medical devices are able to communicate with external devices using wireless communication methods such as radio frequency (RF) or mutual inductance. The external devices are often external programmers that use wireless communication to change performance parameters in the implantable device. Such parameters may interact with each other. For example, programming a first parameter may limit the range of values to which a second parameter can be programmed. Because of this interaction between different programmable parameters, a complex set of constraints typically governs how the set of parameters may be programmed. Consequently, a physician faces a daunting task in programming the whole set of parameters to self-consistent values. Moreover, as new therapies are developed (e.g., congestive heart failure therapies that treat both left and right sides of the heart), more parameters and more interactions between parameters are inevitable, further complicating the task of programming a complete set of parameters to allowable values.

Often, programming one parameter or a set of parameters to a particular value yields invalid results when combined with other interdependent parameter values, causing a complex trial and error analysis for the user. One method of reducing the difficulty of programming parameter values is through establishing manufacturer's default values. This method, however, does not allow the flexibility needed by the physician to tailor a device to treat a particular patient.

To program one or more parameters away from the manufacturer defaults, a user-specified set of parameter values is obtained from the user, and automatically compared to parameter interaction constraints to determine whether a constraint violation has occurred. If no constraint violation exists, the user-specified parameters are accepted into the programmer for programming into the implantable device. However, if a constraint violation does exist, the user may be advised of one or more of the violations. However, it is then typically left to the user to modify the existing set of parameter values to try to remove the violation without inadvertently triggering another violation. This can be a complex process and may decrease the productivity of the user (in most cases a physician), and increase the possibility of programming errors.

OVERVIEW

This document relates generally to systems, devices, and methods for programming an implantable medical device. A system example includes an external device that includes a communication circuit configured to communicate information with an IMD, a programming interface including a display, and a processor communicatively coupled to the communication circuit and the programming interface. The processor includes a parameter analyzer to apply a rule to a combination of operating parameter values of the IND to determine operating parameter interaction. The display includes a first warning that is displayed when the parameter analyzer determines that a combination of operating parameter values entered via the programming interface is not allowed, and a second warning that is displayed when the parameter analyzer determines that a combination of operating parameters values entered via the programming interface is allowable, but is not recommended. The processor is configured to program the operating parameter values associated with the second warning into the ND only after a user acknowledgement of the second warning is received from a user via the programming interface.

A method example includes receiving from a user, at an external device, a combination of operating parameter values for an IMD, applying a rule, using the external device, to the combination of operating parameter values to determine operating parameter interaction, displaying a first warning when a disallowed combination of operating parameter values is received from the user, displaying a second warning when an allowable but not recommended combination of operating parameter values is received from the user, and enabling the combination of operating parameter values associated with the second level warning to be programmed into the IMD only after receiving from the user a user acknowledgement of the second warning.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

This document relates to a user interface for a programmer of an implantable medical device (IMD). To program one or more parameters, a set of parameter values is obtained from the user and automatically compared to parameter interaction constraints to determine whether a constraint violation has occurred. If a constraint violation does exist, the user may be advised of one or more of the violations.

Some violations are more serious than others. The more serious violations are those combinations of parameters that the IMD is not capable of implementing or those combinations that put a patient's safety at risk. These combinations of parameter values are not allowed to be programmed into the IMD. The less serious violations are those combinations of parameters that are allowed, but are not recommended to be programmed into the IMD.

Figure 1:
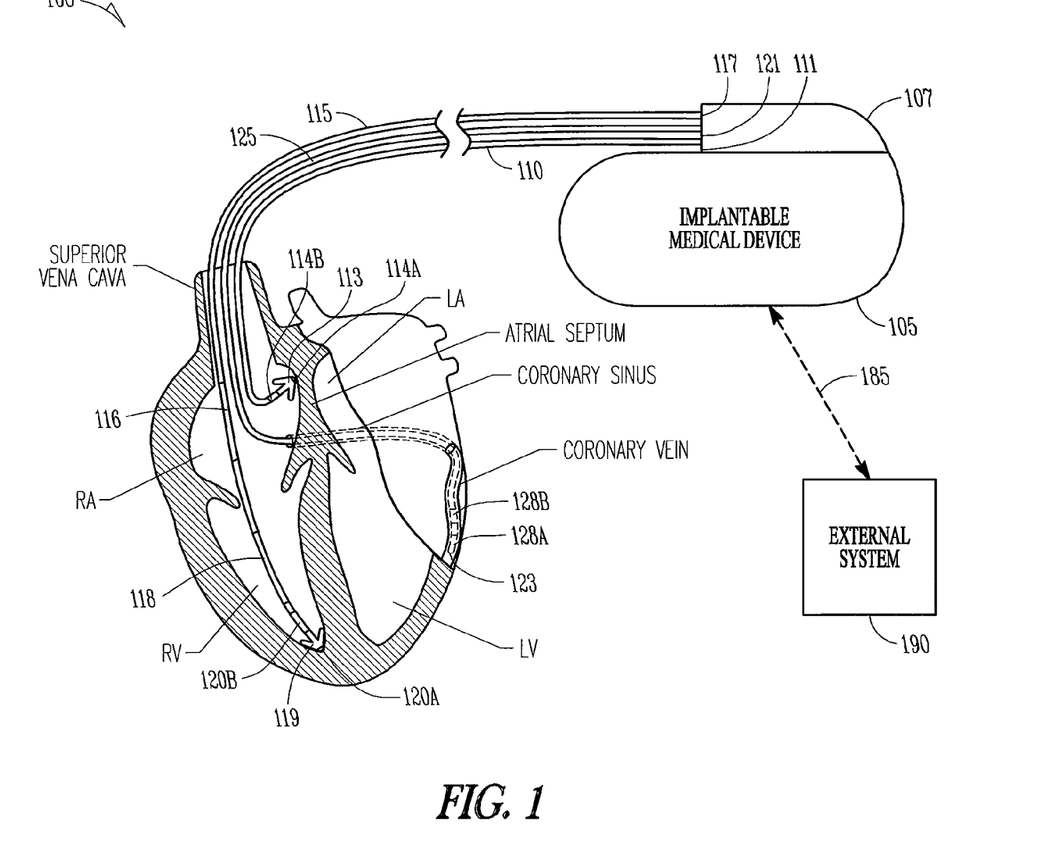
FIG. 1 is an illustration of portions of a system that uses an IMD.

FIG. 1 is an illustration of portions of a system 100 that uses an implantable medical device (IMD) 105. Examples of IMD 105 include, without limitation, a, pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the atrial septum, and are each electrically coupled to IMD 105 through a conductor extending within the lead body. The RA lead is shown placed in or near the atrial septum, but the RA lead may be placed in the atrial appendage or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram indicative of RV depolarizations and delivering RV pacing pulses. RA tip electrode 114A, RA ring electrode 114B, or an electrode formed on the can of IMD 105 allow for sensing an RA electrogram indicative of RA depolarizations and allow for delivering RA pacing pulses. Sensing and pacing allows the IMD 105 to adjust timing of the heart chamber contractions. In some examples, the IMD 105 can adjust the timing of ventricular contractions with respect to the timing of atrial contractions by sensing a contraction in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram indicative of LV depolarizations and delivering LV pacing pulses.

Other forms of electrodes include meshes and patches, which may be applied to one or more portions of heart, or which may be implanted in one or more other areas of the body to help "steer" electrical current produced by the IMD 105 in FIG. 1. The IMDs may be configured with a variety of electrode arrangements or combinations, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of one or more electrical signals related to cardiac activity can provide early, if not immediate, diagnosis of cardiac disease.

Figure 2:
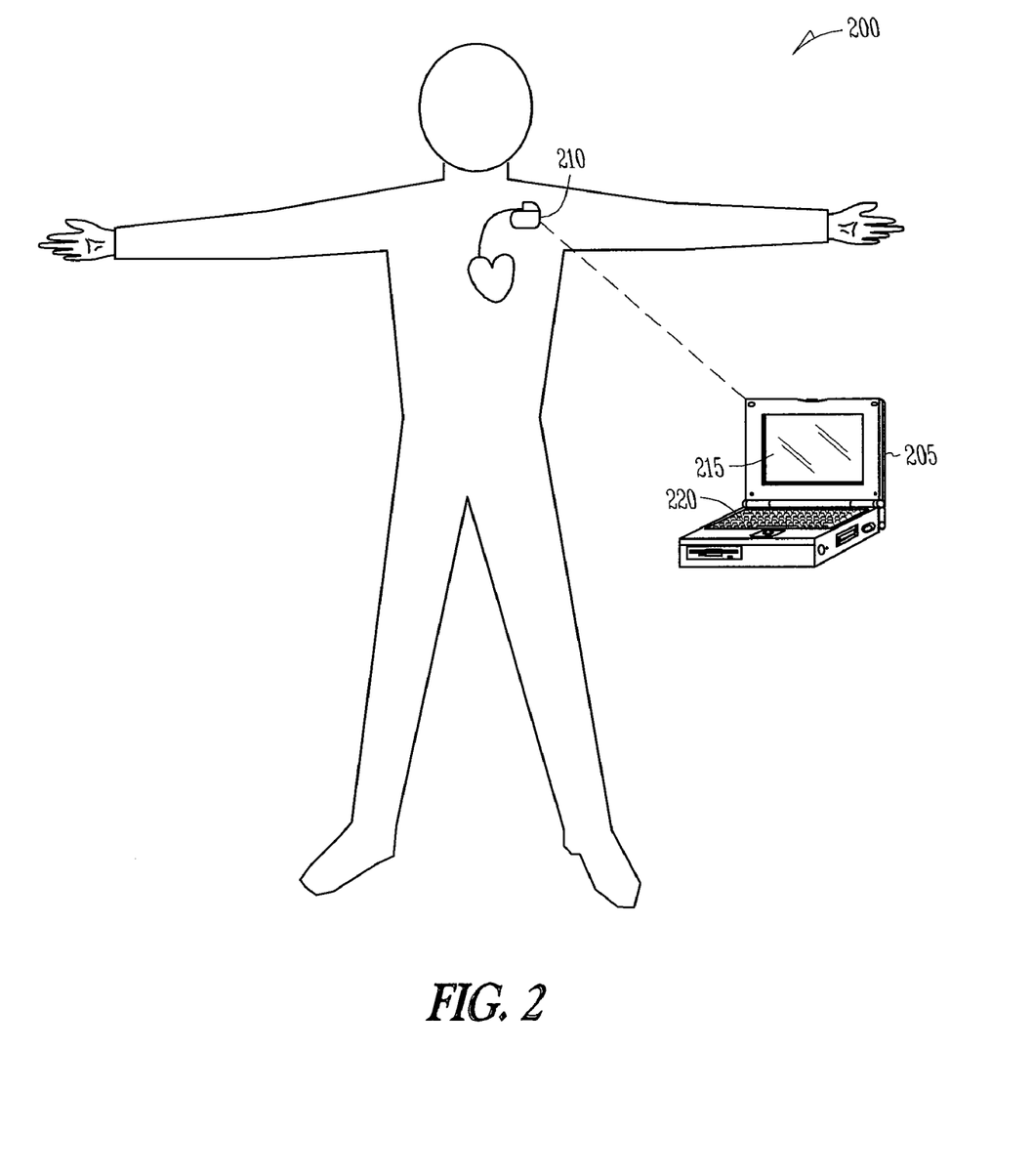
FIG. 2 is an illustration of a system that includes an external device used to program parameters of an IMD.

FIG. 2 is an illustration of a system 200 that includes an external device 205 used to program parameters of an IMD 210. The external device 205 includes a programming interface such as a display 215 and/or a keyboard 220 or computer mouse. The external device 205 communicates with the IMD 210 wirelessly.

Figure 3:
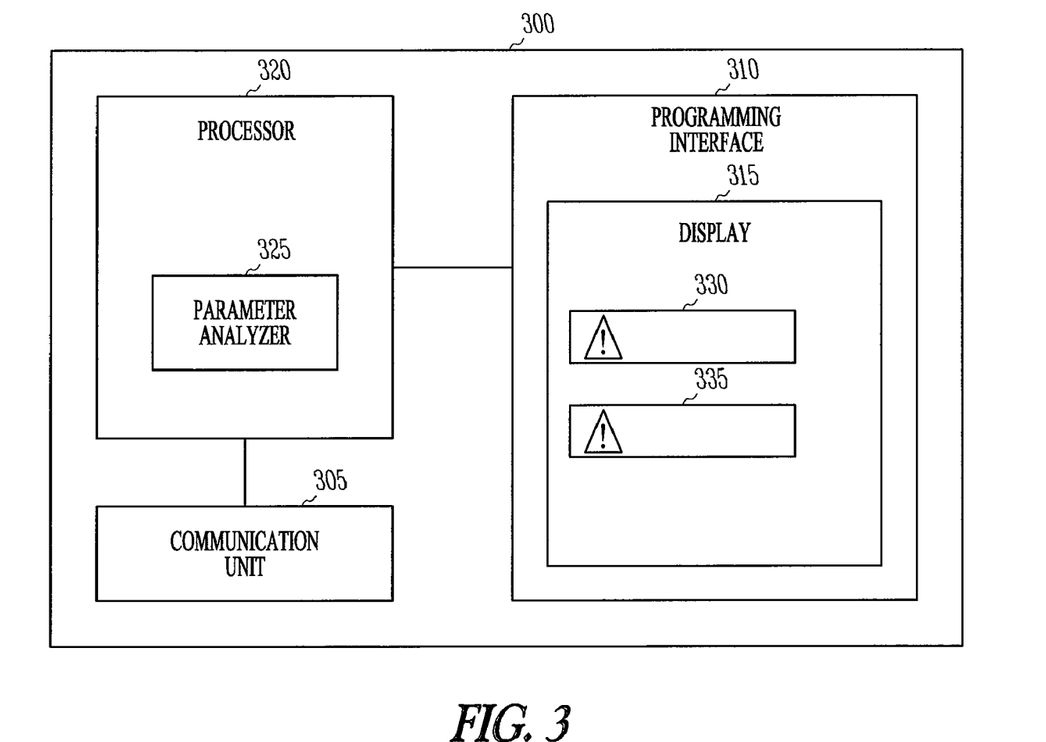
FIG. 3 is a block diagram of an example of a system that includes an external device to program operating parameters into an IMD.

FIG. 3 is a block diagram of an example of a system that includes an external device 300 to program operating parameters into an IMD. The external device 300 includes a communication unit 305 to communicate information with the IMD. The communication unit 305 is configured to facilitate the communication by including any combination of hardware, firmware, or software. The external device 300 includes a programming interface 310, which includes a display 315.

The external device 300 also includes a processor 320 communicatively coupled to the communication unit 305 and the programming interface 310. The processor 320 may include a digital signal processor, application specific integrated circuit (ASIC), microprocessor, or other type of processor, interpreting or executing instructions in software or firmware.

The processor 320 includes a parameter analyzer 325 to apply a rule to a combination of operating parameter values for an IMD to determine operating parameter interaction. A user typically enters or otherwise specifies a first set of desired parameter values for the IMD. The rule applied by the parameter analyzer 325 creates one or more interdependencies between different programmable parameters using a set of parameter interaction constraints. These constraints will restrict which values are acceptable for the user-specified first set of parameter values. The user specified first set of parameter values is automatically checked against such constraints to ensure that the user-specified set of parameter values are acceptable before they are programmed into the IMD. The IMD manufacturer typically defines such restrictions, such as based on safe operating conditions for the IMD. Descriptions of systems, devices, and methods for determining parameter interaction constraints are found in West et al., U.S. patent application Ser. No. 11/380,570, "Medical Device User Interface Automatically Resolving Interaction between Programmable Parameters," filed Apr. 27, 2006 which is incorporated herein by reference.

The automatic comparison of the first set of parameter values to the parameter interaction constraints may result in a first set of one or more constraint violations. In certain examples, the parameter analyzer 325 uses the constraint violations to categorize combinations of operating parameters into multiple categories (e.g., those that are not allowed, those that are allowed but not recommended, and those that are allowed and result in no constraint).

The display 315 includes a first warning 330 that is displayed when a disallowed combination or set of operating parameter values is entered via the programming interface. A combination of operating parameters is not allowed when the combination may result in the IMD functioning incorrectly. For example, if the user tries to program a device lower rate limit (LRL) greater than the maximum tracking rate (MTR), the combination is not allowed. A combination of operating parameters is also not allowed when the parameter analyzer 325 determines that the combination may put a patient's safety at risk. The processor 320 does not allow the operating parameters associated with the first warning 330 to be programmed into the IMD.

The display 315 includes a second warning 335 that is displayed when an allowable but not recommended combination of operating parameter values is entered via the programming interface 310. A combination of operating parameters is allowable but not recommended when the parameter analyzer 325 determines that the combination may result in a reduction in expected efficacy of therapy or diagnostics provided by the IMD.

In certain examples, the first warning 330 includes a display of the word "error" or "warning," while the second warning 335 includes a display of the word "attention." In certain examples, the display 315 uses a first color to display the first warning 330 (e.g., red) and a different second color to display the second warning 335 (e.g., yellow). In certain examples, the display 315 inhibits the display of the operating parameter values associated with the first warning or the second warning when displaying at least one of the first warning and the second warning. In certain examples, the display 315 alters the display of the operating parameter values associated with the first warning 330 or the second warning 335 when displaying at least one of the first warning and the second warning. For instance, the display 315 may "ghost" or the operating parameter values by displaying the parameters at a lower intensity.

The second warning 335 may be overridden. The processor 320 programs the operating parameter values associated with the second warning 335 into the IMD only after a user acknowledgement of the second warning is received from a user via the programming interface. Without the acknowledgement from the user, the operating parameter values associated with the second warning 335 are treated as not allowed and are not programmed into the IMD. This programming limitation prevents the user from pushing past the conflicts in the selected set of operating parameters until the user overrides the limitation by acknowledging and accepting the patient risk. In certain examples, the operating parameters are not displayed until the user acknowledges and accepts the patient risk. In certain examples, the operating parameters are ghosted until the user acknowledges and accepts the patient risk.

According to some examples, the second warning 335 includes text. The processor 320 programs the operating parameter values associated with the second warning 335 into the IMD only after receiving an acknowledgement of the second warning 335 that indicates the user read the text. The processor 320 may receive the acknowledgement via the programming interface 310 such as by a keyboard, keypad, touch screen, computer mouse, or the like. In certain examples, the second warning 335 includes educational text concerning a risk to the patient from the entered combination of operating parameters.

Figure 4:
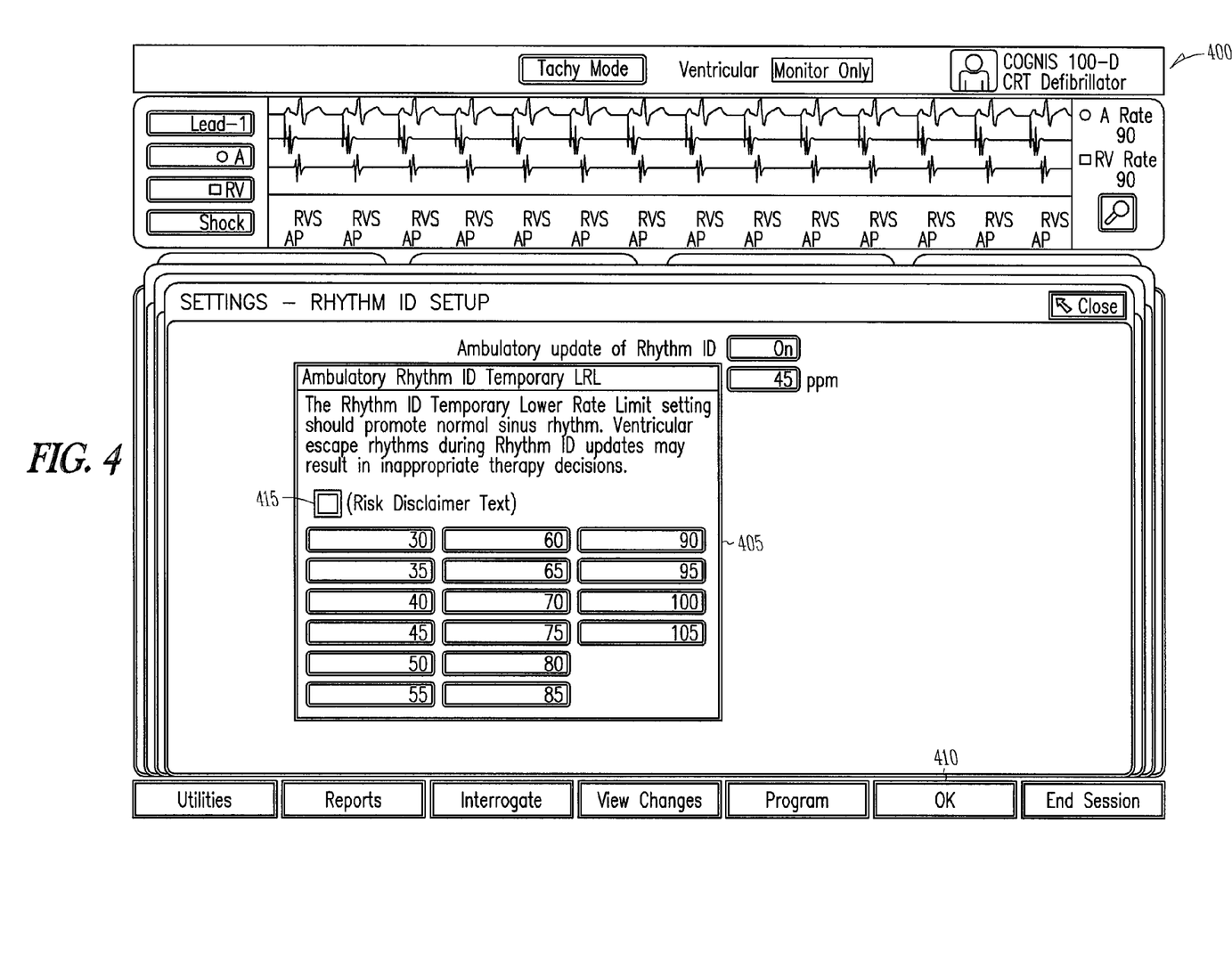
FIG. 4 is an illustration of an example of a programming interface display screen for an external device used to program an IMD.

FIG. 4 is an illustration of an example of a programming interface display screen 400 for an external device used to program an IMD. The example shows a user selecting a Rhythm ID Temporary Lower Rate Limit of 45 pulses per minute (ppm). When a user attempts to program an operating parameter, a text box 405 containing educational text concerning the IMD parameter is displayed. The display may include an indication that there is no risk to the patient caused by the selection. For example, the display screen 400 may display an OK indication 410. In certain examples the indication is displayed using a color (e.g., green) different from a color used to display a violation. Because the selection does not result in risk or other violation, the user is not required to check a risk disclaimer box 415 before programming the parameter into the IMD.

Figure 5:
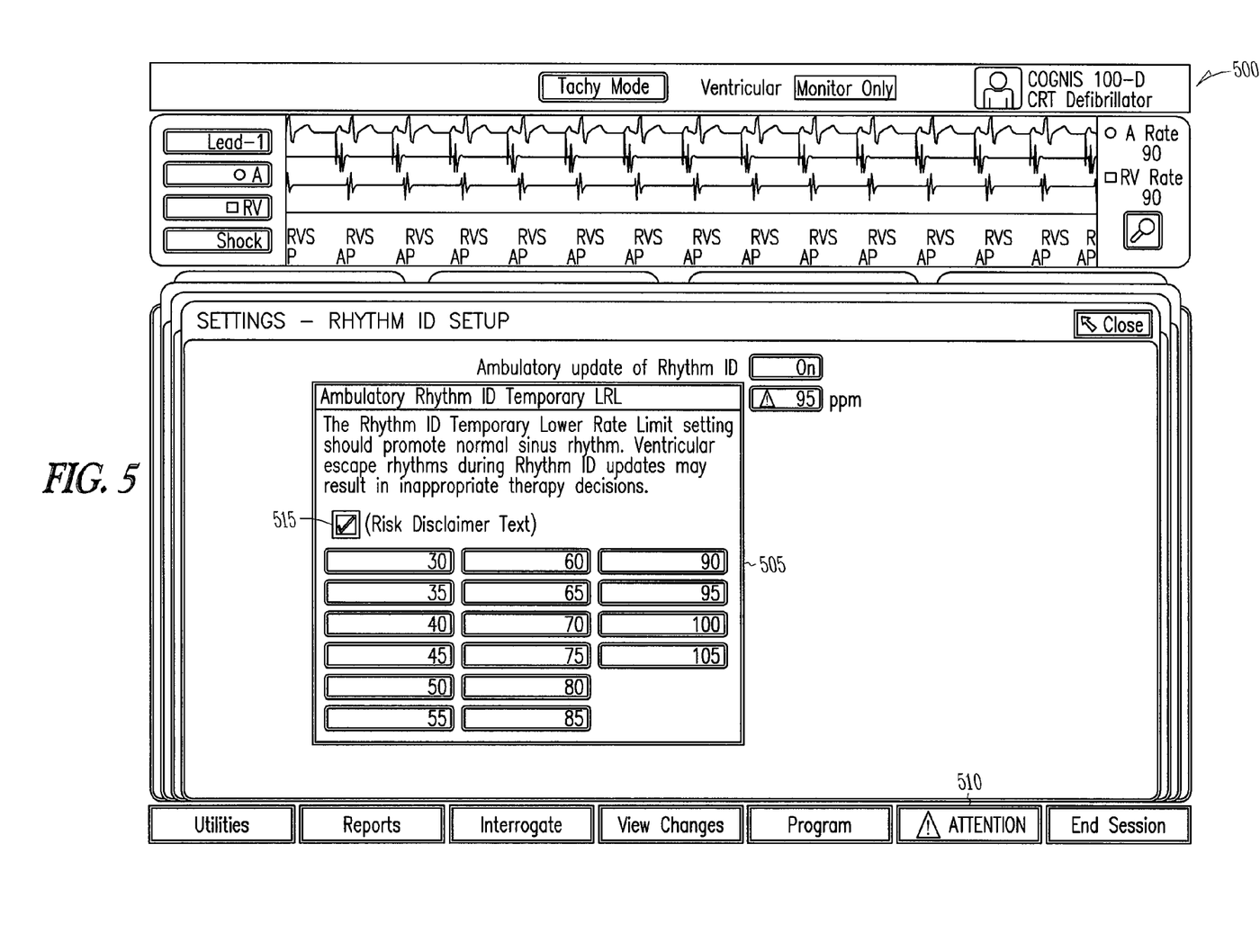
FIG. 5 is an illustration of another example of a programming interface display screen for an external device used to program an IMD.

FIG. 5 is an illustration of another example of a programming interface display screen 500 for an external device used to program an IMD. The example shows a user selecting a Rhythm ID Temporary Lower Rate Limit of 95 ppm. A text box 505 containing educational text concerning the IMD parameter is displayed. The display screen includes a warning 510 that the selection results in a combination of operating parameter values that are allowable but not recommended. Because the selection may result in risk to the patient, the user is required to check the risk disclaimer box 515 before the parameter or parameters are allowed to be programmed into the IMD.

For example, the user may be selecting a set of operating parameters that sacrifices bradycardia pacing for tachyarrhythmia sensing. The text informs the user of the IMD operation and the user can make an informed decision about whether to program more pacing at the expense of tachy sensing, or more tachy sensing with less pacing. The text includes an explanation of the risk involved in the programming and is displayed at the time of parameter selection. The user then actively chooses between the risks involved to provide the best therapy for the patient using their professional judgment.

Figure 6:
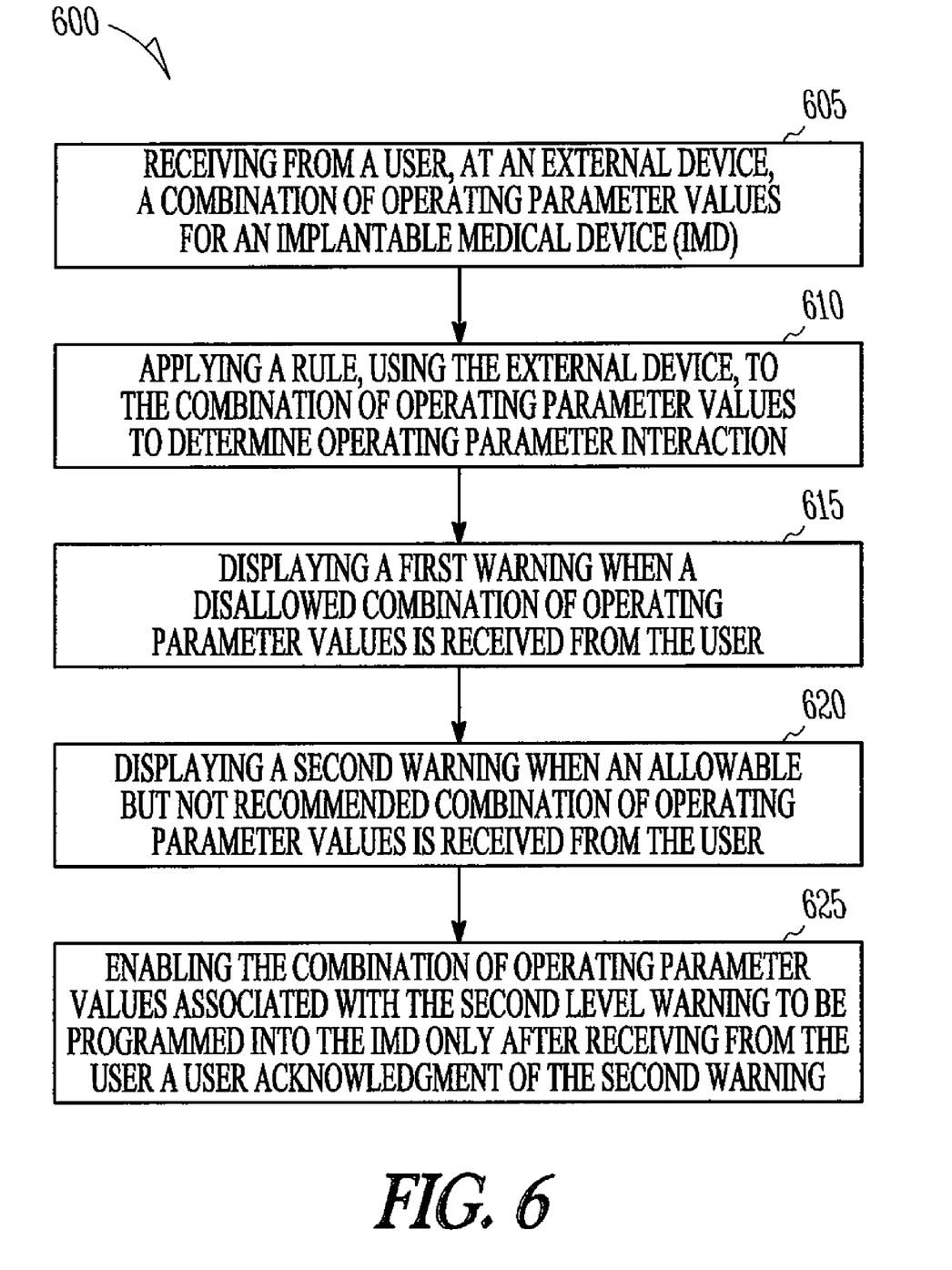
FIG. 6 shows a flow diagram of an example of a method of overriding programming limitations on operating parameters for an IMD.

FIG. 6 shows a flow diagram of an example of a method 600 of overriding programming limitations on operating parameters for an IMD. At block 605, a combination of operating parameter values for an IMD is received from a user at an external device. At block 610, using the external device, a rule is applied to the combination of operating parameter values to determine operating parameter interaction. At block 615, a first warning is displayed when a disallowed combination of operating parameter values is received from the user. At block 620, a second warning is displayed when an allowable but not recommended combination of operating parameter values is received from the user at the external device. At block 625, the combination of operating parameter values associated with the second level warning is enabled to be programmed into the IMD only after receiving from the user a user acknowledgement of the second warning.

Figure 7:
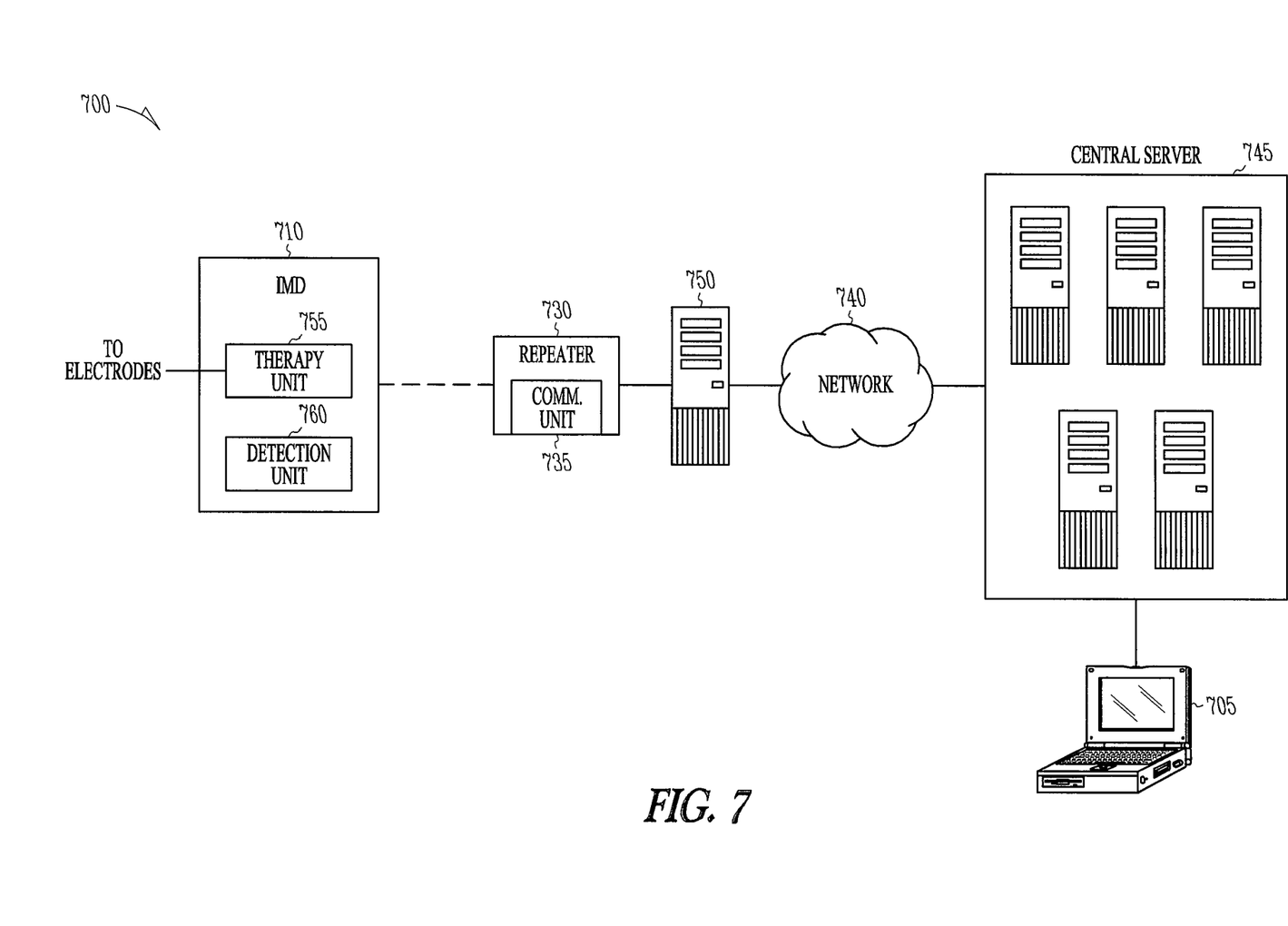
FIG. 7 shows a block diagram of another example of a system to program operating parameters into an IMD.

According to some examples, the programming interface is remote from the IMD. FIG. 7 shows a block diagram of another example of a system 700 to program operating parameters into an IMD 710. The system 700 includes a repeater 730 and an external device 705. The repeater 730 includes a communication unit 735 configured to communicate information with the IMD 710 and the external device 705. The repeater 730 is local to the IMD 710, such as by being in the same room as the patient for example. In the example shown, the repeater 730 communicates with the external device 705 via a computer network 740. The external device 705 may access the computer network 740 through a central server 745. The repeater 730 may access the computer network 740 through a local computer 750. In certain examples, the repeater 730 communicates with the external device 705 via a cell phone network.

The external device 705 includes a programming interface to program operating parameters into the IMD 710. In certain examples, the IMD 710 includes a therapy unit 755 configured to provide bradycardia pacing therapy and/or cardioversion/defibrillation therapy to a patient, and a detection unit 760 to detect tachyarrhythmia in the patient.

Returning to the external device 300 of FIG. 3, in some examples, the parameter analyzer 325 determines that a combination of operating parameter values is not allowed and/or determines that a combination is allowable but not recommended using information about whether the programming interface 310 is local to or remote from the IMD. The programming interface is local to the IMD when the external device 300 communicates with the IMD directly. The programming interface 310 is remote from the IMD when the external device 300 communicates with the IMD using a third device such as the repeater shown in FIG. 7.

In certain examples, the parameter analyzer 325 may determine that an operating parameter set selected by a user is not allowed whether programmed in a clinical setting or programmed remotely. In an illustrative example, the user may try to set the minimum dynamic ventricular refractory period plus 90 milliseconds (Min Dynamic VRP+90 ms) greater than the upper rate limit (URL) in ms. Such a combination places the patient's safety at risk and would not be allowed by the rule applied by the parameter analyzer 325 whether selected in a clinical setting or selected remotely.

In certain examples, the parameter analyzer 325 may determine that an operating parameter set selected by a user is allowable but not recommended when in a clinical setting and not allowed when selected remotely. As an illustrative example, a user may select an operating parameter set that reduces the right ventricle (RV) pacing amplitude by 25%. Reducing the RV pacing amplitude may result in the IMD not providing ventricular contractions. This may be allowable in a clinical setting because the clinician may easily observe whether the programming affects the patient adversely, such as by causing syncope for example. Thus, the parameter analyzer 325 identifies a different combination of operating parameters as being allowable but not recommended when the programming is in a clinical setting and the external device 300 communicates with the IMD directly than when the programming is remote. In another illustrative example, the user selects to extend the atrial-ventricular delay (A-V Delay) to such an extent that pacing by the IMD is inhibited. This may also be deemed by the parameter analyzer 325 to be allowable but not recommended in a clinical setting and not allowed when programmed remotely.

In some examples, the first warning 330 and the second warning 335 include text, and the text content is a function of whether the programming interface is local to the NMD in a clinical setting or remote from the ND. In the illustrative example above, the first warning displayed when a user remotely programs a reduced RV pacing amplitude by 25% may include text explaining that the programming is not allowed to the risk of syncope in the patient. Such text may not be included in the second warning displayed when the programming is in a clinical setting.

The clinician is allowed to program the operating parameters after the external device 300 displays the second warning 335 and the clinician acknowledges the risk, thereby allowing the clinician to use their professional judgment in programming the device. Note that because the same combination of parameters may be allowable in a clinical setting but not allowed in a remote setting, the constraints determined by the parameter analyzer 325 may result in more first warnings 330 for a remote programming session than for a programming session in a clinical setting.

In certain examples, the parameter analyzer 325 may determine that an operating parameter combination selected by a user is allowable but not recommended when selected either remotely or in a clinical setting. As an illustrative example, a user may select an operating parameter combination that sets a tachyarrhythmia rate detection zone interval (ms) greater than the lower rate limit interval (ms) minus the atrial-ventricular delay (Tachy Rate Zone interval>LRL−AV Delay). Such an operating parameter set would cause the IMD to provide pacing pulses within the Tachy Rate Zone and would be allowable but not recommended whether in a clinical setting or when programming remotely.

In certain examples, the parameter analyzer 325 may determine that an operating parameter set selected by a user is allowed when in a clinical setting and allowable but not recommended when selected remotely. As an illustrative example, a current set of operating parameter values may include a LRL of 60 ppm and a user may select to reduce the LRL by 15%. Because reducing the LRL may compromise efficacy of the IMD, this selection may be allowed in a clinical setting, but may be deemed allowable but not recommended when programming remotely. In a clinical setting the display 315 may display an OK indication. In a remote programming setting, the user is allowed to program the operating parameters after the external device 300 displays the second warning 335 and the clinician acknowledges the risk. Note that the constraints determined by the parameter analyzer 325 may result in more second warnings 335 for a remote programming session than for a programming session in a clinical setting.

Information as to whether the programming interface 310 is local to or remote from the IND can be furnished by the user or can be obtained by the external device 300 at the time of the programming. For example, the external device 300 may transmit a message and a receiving device identifies itself in a response message. In some examples, the parameter analyzer 325 includes more than one rule to apply to operating parameters to determine constraints, and applies a different rule when the external device 300 is local to the IMD than when the external device is remote from the external device 300.

The parameter analyzer 325 identifies parameter interaction constraints that may result in a first set of one or more constraint violations. The external device 300 uses the constraints to limit the combination of operating parameters available to the user. The constraint violations and thus the combination limits may vary depending on whether the parameters are being programmed in a local or a remote programming session. The external device 300 provides a flexible interactive limit override for the operating parameters. Flexible interactive limit control improves patient safety and promotes conscious decision making from physicians when the patient's condition may cause the physician to desire conflicting device settings.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising an external device including:
   a communication unit configured to communicate information with an implantable medical device (IMD);
   a programming interface including a display; and
   a processor communicatively coupled to the communication circuit and the programming interface, wherein the processor includes:
   a parameter analyzer configured to apply a rule to a combination of operating parameter values of the IMD to determine operating parameter interaction; and wherein:
   the display includes a first warning that is displayed when the parameter analyzer determines that a combination of operating parameter values entered via the programming interface is not allowed;
   the display includes a second warning that is displayed when the parameter analyzer determines that a combination of operating parameters values entered via the programming interface is allowable but not recommended, the second warning including text identifying a specific risk reason why the combination of operating parameter values is allowable but not recommended, and wherein the combination of operating parameters values that is allowable but not recommended and the text content of the second warning are a function of whether the programming interface is local to or remote from the IMD; and
   the processor is configured to enable programming of the allowable but not recommended combination of operating parameter values associated with the second warning into the IMD only after a user overrides the second warning by affirmatively acknowledging having read the second warning, wherein the acknowledgement of the second warning is received from the user via the programming interface.

2. The external device of claim 1, wherein the text identifying a specific risk reason why the combination of operating parameter values is allowable but not recommended includes educational text concerning a risk to the patient from the entered combination of operating parameters.

3. The external device of claim 1, wherein the parameter analyzer is configured to determine that a combination of operating parameter values is an allowable but not recommended combination of operating parameter values based on an expected efficacy of a therapy provided by the IMD.

4. The external device of claim 1, wherein the display uses a first color to display the first warning and a different second color to display the second warning.

5. The external device of claim 1, wherein the display is configured to alter display of the operating parameter values associated with the first warning or the second warning when displaying at least one of the first warning and the second warning.

6. The external device of claim 1, wherein the display is configured to inhibit display of the operating parameter values associated with the first warning or the second warning when displaying at least one of the first warning and the second warning.

7. The system of claim 1, including a repeater, wherein the repeater includes a communication circuit configured to communicate information with the IMD and the external device, and wherein the processor is configured to display different text with the second warning when the external device communicates with the IMD via the repeater than when the external device communicates with the IMD directly.

8. The system of claim 1, including the IMD and a repeater, wherein the repeater includes a communication unit configured to communicate information with the IMD and the external device, and wherein the parameter analyzer is configured to categorize a different combination of operating parameters as being allowable but not recommended when the external device communicates with the IMD via the repeater than when the external device communicates with the IMD directly.

9. The system of claim 8, wherein the IMD provides a therapy to a patient, and wherein the parameter analyzer is configured to categorize a combination of operating parameter values as being allowable but not recommended when the combination of operating parameter values results in reduced efficacy of the therapy.

10. The system of claim 9, wherein the IMD includes a therapy unit configured to provide at least one of bradycardia pacing therapy and cardioversion/defibrillation therapy, and a detection unit configured to detect tachyarrhythmia.

11. A method comprising:
receiving from a user, at an external device, a combination of operating parameter values for an implantable medical device (IMD);
applying a rule, using the external device, to the combination of operating parameter values to determine operating parameter interaction;
displaying a first warning when a disallowed combination of operating parameter values is received from the user;
displaying a second warning when an allowable but not recommended combination of operating parameter values is received from the user, the second warning including text identifying a specific risk reason why the combination of operating parameter values is allowable but not recommended, and wherein the combination of operating parameters values that is allowable but not recommended and the text content of the second warning are a function of whether a programming interface of the external device is local to or remote from the IMD; and
enabling the combination of allowable but not recommended operating parameter values associated with the second level warning to be programmed into the IMD only after affirmatively acknowledging having read the second warning via the programming interface of the external device to override the second warning.

12. The method of claim 11, wherein displaying the text includes displaying educational text concerning risk to the patient resulting from the combination of operating parameter values associated with the second warning.

13. The method of claim 11, comprising selecting the rule as a function of whether the external device is local to or remote from the IMD.

14. The method of claim 11, comprising excluding a combination of operating parameter values from a recommended set of operating parameter values based on an expected efficacy of the combination of operating parameter values.

15. An apparatus comprising:
means for receiving from a user, at an external device, a combination of operating parameter values for an implantable medical device (IMD);
means for applying a rule, using the external device, to the combination of operating parameter values to determine operating parameter interaction;
means for displaying a first warning when a disallowed combination of operating parameter values is received from the user;
means for displaying a second warning when an allowable but not recommended combination of operating parameter values is received from the user, the second warning including text identifying a specific risk reason why the combination of operating parameter values is allowable but not recommended, and wherein the combination of operating parameters values that is allowable but not recommended and the text content of the second warning are a function of whether a programming interface of the external device is local to or remote from the IMD; and
means for enabling the combination of allowable but not recommended operating parameter values associated with the second level warning to be programmed into the IMD only after affirmatively acknowledging having read the second warning via the programming interface of the external device to override the second warning.

* * * * *